United States Patent [19]

Temple, Jr. et al.

[11] 4,456,756

[45] Jun. 26, 1984

[54] SPIROTHIAZOLIDINYL PIPERAZINE DERIVATIVES

[75] Inventors: Davis L. Temple, Jr.; Richard E. Yeager, both of Evansville, Ind.

[73] Assignee: Mead Johnson & Company, Evansville, Ind.

[21] Appl. No.: 289,351

[22] Filed: Aug. 3, 1981

[51] Int. Cl.³ .............................................. C07D 417/06
[52] U.S. Cl. ..................................... 544/364; 546/284; 548/147; 424/250; 424/270; 544/369; 544/360; 544/392
[58] Field of Search ............... 544/369, 230, 270, 364; 546/284; 548/147; 424/250

[56] References Cited

U.S. PATENT DOCUMENTS

| | | | |
|---|---|---|---|
| 3,106,552 | 10/1963 | Grogan et al. | 546/15 |
| 3,200,118 | 8/1965 | Grogan et al. | 546/15 |
| 3,398,151 | 8/1968 | Wu | 544/230 |
| 3,432,499 | 3/1969 | Rice et al. | 544/230 |
| 3,717,634 | 2/1973 | Wu et al. | 544/230 |
| 4,367,335 | 1/1983 | Temple | 424/250 |

OTHER PUBLICATIONS

Wu, et al., "Psychosedative Agents . . ." *J. Med. Chem.*, 12, 876–881 (1969).
Wu, et al., "Psychosedative Agents 2 . . ." *J. Med. Chem.* 15, 477–479 (1972).
Jones, et al., "Some 5 Spirothiazolidiones" *J. Chem. Soc.*, London, 91–92 (1946).

*Primary Examiner*—Donald G. Daus
*Assistant Examiner*—G. Hendricks
*Attorney, Agent, or Firm*—Robert H. Uloth; Richard P. Ryan

[57] ABSTRACT

Piperazinyl derivatives containing a spiro-2,4-thiazolidinedione heterocyclic component with relatively selective psychotropic properties are disclosed. The compound 2-[4-[4-(7,9-dioxo-6-thia-8-azaspiro[4.4]nonan-8-yl)butyl]-1-piperazinyl]pyridine-3-carbonitrile which has selective anti-psychotic activity constitutes a typical embodiment of the invention.

5 Claims, No Drawings

SPIROTHIAZOLIDINYL PIPERAZINE DERIVATIVES

BACKGROUND OF THE INVENTION

This invention generally pertains to heterocyclic carbon compounds having drug and bio-affecting properties and to their preparation and use. In particular, the invention is concerned with 1,4-disubstituted piperazine derivatives wherein one substituent is "4-(7,9-dioxo-6-thia-8-azaspiro[4.4]nonan-8-yl)butyl" and the other an "aryl or pyridinyl" radical. As used herein, "7,9-dioxo-6-thia-8-azaspiro[4.4]nonan-8-yl" refers to the radical derived from the compound "5-spirocyclopentyl-2,4-thiazolidinedione" structurally depicted below with positions numbered in accordance with employed nomenclature.

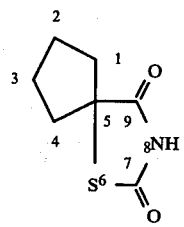

Thiazolidinediones are known to the art. For example, Jones, et al., J. Chem. Soc., London, 91–92 (1946) refer to 5,5-dialkyl-2,4-thiazolidinedione barbituric acid analogs and disclose that a 5-spirocyclohexyl-2,4-thiazolidinedione (1) produced narcosis and analgesia in mice.

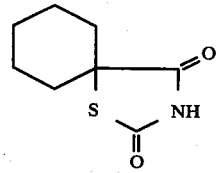

Various types of 1,4-substituted piperazine derivatives are also known to the art as illustrated in the following references.

Great Britain No. 2,023,594A discloses 1-(R-alkyl)-4-(3-trifluoromethylthiophenyl)piperazines useful for treating anxiety and depression having general formula (2)

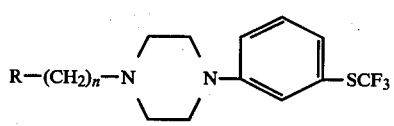

wherein n is 1–3 and R inter alia represents heterocycles such as

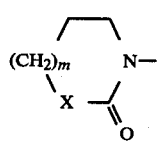

wherein m is 0 or 1 and X is a —S—, —O—, imino, alkyl-imino or methylene.

Wu, U.S. Pat. No. 3,398,151, Wu, et al., U.S. Pat. No. 3,717,634 and, respective, corresponding Wu, et al., publications—J. Med. Chem., 12, 876–881 (1969), 15, 477–479 (1972)—variously describe psychotropic compounds resembling formula (3)

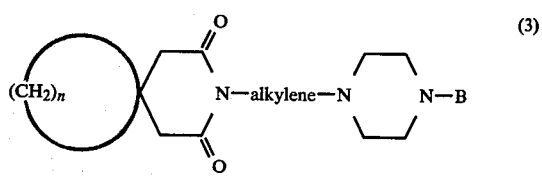

wherein n is 4 or 5 and B inter alia represents phenyl plus various heterocycles (all with optional substituents):

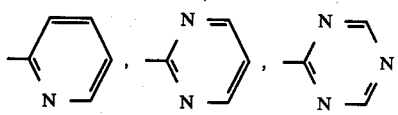

Casten, et al., U.S. Pat. No. 4,182,763 concerns the anxiolytic use of compound (4) which is referred to in the biological literature as buspirone.

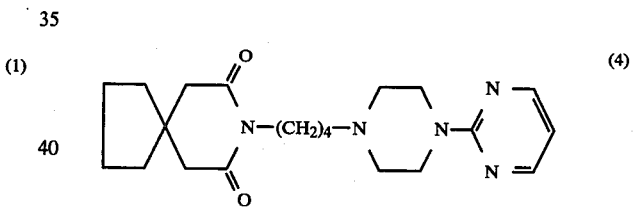

Palazzo, U.S. Pat. No. 3,857,845 describes the compound (5) as having typical tranquilizing properties.

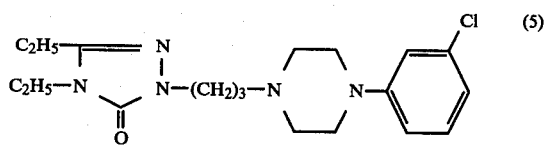

None of the aforementioned references disclose or suggest piperazine derivatives containing the 2,4-thiazolidinedione heterocyclic component of the subject compounds of this invention.

SUMMARY OF THE INVENTION AND DESCRIPTION OF PREFERRED EMBODIMENTS

In its broadest aspect, the present invention is concerned with spirothiazolidinediones characterized by Formula I

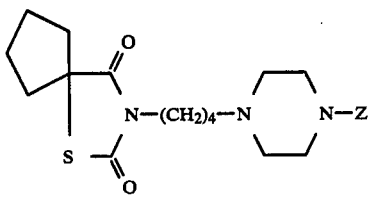

wherein Z is a $R_1$-substituted phenyl having the formula

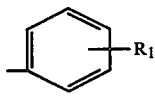

in which $R_1$ is hydrogen, halogen, lower alkyl, lower alkoxy or trifluoromethyl, a $R_2$-substituted 2-pyridinyl radical having the formula

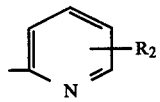

in which $R_2$ is hydrogen or cyano, or a pharmaceutically acceptable non-toxic acid addition salt thereof.

It is to be understood that, as used herein, halogen comprehends fluorine, bromine, iodine and preferably chlorine with the terms "lower alkyl" and "lower alkoxy" referring to both straight and branched chain carbon radicals of from 1 to 4 carbon atoms inclusive. Illustrative of these radicals are carbon chains which can be methyl, ethyl, propyl, isopropyl, 1-butyl, 1-methylpropyl and 2-methylpropyl.

The pharmaceutically acceptable acid addition salts of the invention are those in which the anion does not contribute significantly to the toxicity or pharmacological activity of the salt and, as such, they are the pharmacological equivalents of the bases of Formula I. They are generally preferred for medical usage. In some instances, they have physical properties which make them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of the base of Formula I with the selected acid preferably by contact in solution employing an excess of commonly used inert solvents such as water, ether, benzene, ethanol, ethyl acetate and preferably acetonitrile. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include sulfuric, phosphoric, hydrochloric, hydrobromic, hydroiodic, citric, acetic, benzoic, cinnamic, mandelic, phosphoric, nitric, mucic, isethionic, palmitic, heptanoic, and others.

According to the present invention, general embodiments of the process for preparing compounds characterized by Formula I are illustrated by the following reaction schemes.

Method A

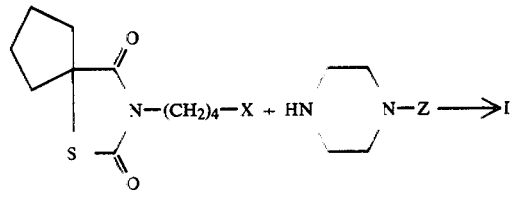

Method B

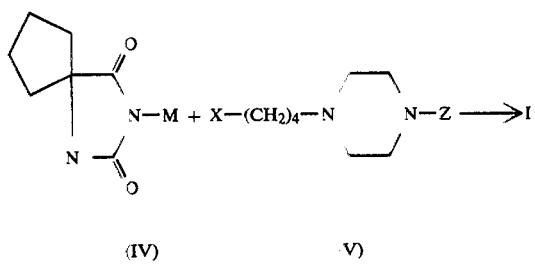

In the foregoing (II-V) formulas, the symbol "Z" is as defined above with respect to Formula I with "X" representing the acid residue of a reactive ester grouping such as chloride, bromide, iodide, fluoride, sulfate, phosphate, tosylate or mesylate. The symbol "M" represents an alkali metal salt of the thiazolidinedione such as sodium, potassium and lithium.

Method A is conventionally carried out under reaction conditions employed in preparing tertiary amines by alkylating secondary amines. Thus, the compounds of Formula I are obtained by reacting a 3-(4-X-butyl)-spiro-2,4-thiazolidinedione of Formula (II) in an inert reaction medium at temperatures of from about 50° to about 200° C. with a Formula (III) "Z-piperazine" in the presence of a base suitable for use as an acid binding agent. Operable inorganic and organic acid binding bases include tertiary amines, alkali and alkaline earth metal carbonates, bicarbonates, or hydrides with sodium carbonate and potassium carbonate particularly preferred. As referred to herein, the term "inert reaction medium" is meant any protic or aprotic solvent or diluent which does not enter into the reaction to any substantial degree. In this regard, acetonitrile is a particularly preferred solvent with the reaction conveniently carried out at reflux temperature. Satisfactory yields of the present compounds are obtained with reaction periods ranging from about 2-24 hours. Formula (I) products may be purified by crystallization techniques from standard solvent media such as acetonitrile, isopropanol, ethanol and the like and by other conventional methods such as chromatography employing a silica gel column with mixtures of chloroform and alkanols such as methanol and ethanol as eluant.

Method B illustrates another modification of the instant process for preparation of Formula I compounds. In this method, the spiro-2,4-thiazolidine alkali metal salt (IV) is reacted with a piperazinylbutyl halide or ester of Formula (V). Standard laboratory procedures are employed in carrying out this reaction such as those described for the alkylation step of the Gabriel synthesis—S. Gabriel, Ber. 20, 2224 (1887). In the present case, for instance, the reactants are combined in an inert reaction medium at temperatures ranging from 50° C. to 200° C. Toluene and xylene are particularly preferred solvents for carrying out the reaction but other solvents which do not adversely affect the reaction or reactants can be employed. In this regard, solvents such as dioxane, benzene, dimethylformamide, acetone, acetonitrile, n-butanol and the like are operable. In general, the alkali metal salts (IV) are prepared by treating the corresponding spiro-2,4-thiazolidinedione with an alkali hydride such as sodium hydride, an alkali alcoholate such as sodium ethoxide, an alkali amide such as sodium amide, or alkali base such as sodium hydroxide or potassium hydroxide in a suitable solvent.

With respect to reactants (II-V), many are known compounds available from commercial sources or can be prepared in accordance with standard synthetic procedures. For example, preparation of the 5-spirocyclopentyl-2,4-thiazolidinedione intermediate required for preparation of the spiro-2,4-thiazolidinedione butyl halide reactants of Formula (II) and metal salts of Formula (IV) is described by E. R. H. Jones, et al., supra. Conversion of the spiro-2,4-thiazolidinedione to the alkali metal salt (IV) as described above and alkylation with X—(CH$_2$)$_4$—X wherein "X" is as defined above in a reaction inert medium such as dimethylformaide affords the 3-(X-butylene)-2,4-3-(4-X-butyl)-spirocyclopentyl-2,4-thiazolidinedione (II).

Appropriate piperazine reactants (III) and (V) for Methods A and B are obtained in accordance with standard synthetic procedures employed by those skilled in the art for preparation of similar type compounds. C. B. Pollard, et al., J. Org. Chem., 24, 764-767 (1959), Plazzo, et al. U.S. Pat. No. 3,381,009 and Wu, et al., U.S. Pat. No. 3,717,634 all describe methods applicable for the preparation of such compounds and the aforementioned patents are incorporated herein by reference.

The foregoing general embodiments illustrated by Methods A and B constitute a unitary process for preparing compounds of Formula (I) which comprises reacting a spiro-2,4-thiazolidinedione of Formula (VI)

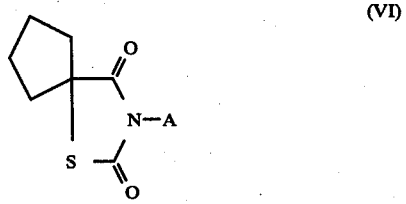

(VI)

with a piperazine of Formula (VII)

(VII)

wherein A is independently and appropriately hydrogen, an alkali metal salt or the radical X—(CH$_2$)$_4$— and the symbols "X and Z" are as defined above.

The Formula (I) compounds are useful pharmacological agents with psychotropic properties. In this regard, they exhibit selective central nervous system activity at non-toxic doses and as such are useful as neuroleptic (antipsychotic) and/or anxiolytic agents. That is to say they produce certain responses in standard in vivo and in vitro pharmacological test systems known to correlate well with relief of anxiety and symptoms of acute and chronic psychosis in man. The following are illustrative of such conventional in vivo test systems used to classify and differentiate a psychotropic agent from a nonspecific CNS depressant and determine potential side-effect liabilities.

| Behavioral Test | Reference |
|---|---|
| Suppression of conditioned avoidance response (CAR) | Albert, Pharmacologist, 4, 152 (1962); Wu et al., J. Med. Chem., 12, 876-881 (1969). |
| Catalepsy | Costall, et al., Psychopharmacologia, 34, 233-241 (1974); Berkson, J. Amer. Statist. Assoc., 48, 565-599 (1953). |
| Fighting Mouse | Tedeschi, et al., J. Pharmacol. Expt. Therap., 125, 28 (1959). |
| Rotarod | Kinnard, et al., J. Pharmacol. Expt. Therap., 121, 354 (1957). |

As further indication of the psychotropic activity and specificity of the instant compounds, state of the art in vitro central nervous system receptor binding methodology can be employed. Certain compounds (commonly referred to as ligands) have been identified which preferentially bind to specific high affinity sites in brain tissue dealing with psychotropic activity or potential for side effects. Inhibition of radiolabeled ligand binding to such specific high affinity sites is considered a measure of a compound's ability to affect corresponding central nervous system function or cause side effects in vivo. This principal is employed in the following assays which are given by way of example.

| Receptor Binding Assay | Reference |
|---|---|
| Dopamine | Burt, et al., Molec. Pharmacol., 12, 800 (1976); Science, 196, 326 (1977); Creese, et al, Science, 192, 481 (1976). |
| Cholinergic | Yamamura, et al., Proc. Natn. Acad. Sci. USA 71 1725 (1974). |
| Alpha-receptor | Crews, et al., Science 202: 322 (1978). Rosenblatt, et al., Brain Res. 160: 186 (1979) U'Prichard, et al., Science 199: 197 (1978). U'Prichard, et al., Molec. Pharmacol. 13: 454 (1977). |
| Serotonin Type 2 | Peroutka and Snyder, Molec. Pharmacol. 16: 687 (1979). |

According to the pharmacological profile established by the aforementioned tests, the instant compounds of Formula (I) have promising anti-psychotic and/or anxiolytic potential. Regarding selective anti-psychotic activity, 2-[4-[4-(7,9-dioxo-6-thia-8-azaspiro[4.4]nonan-8-yl)butyl]-1-piperazinyl]pyridine-3-carbonitrile is a particularly preferred compound in that CAR is suppressed in the rat with significant dopamine receptor binding activity. Regarding side effects, this compound does not produce significant catalepsy in the rat indicating a relative lack of extrapyramidal reactions and further reverses previously established phenothiazine-induced catalepsy in the rat. The latter action indicates that 2-[4-[4-(7,9-dioxo-6-thia-8-azaspiro[4.4]nonan-8-yl)butyl]-1-piperazinyl]pyridine-3-carbonitrile is an effective agent with respect to treating extrapyramidal symptoms and is potentially useful in treating tardive dyskinesia.

As previously mentioned, the instant compounds have psychotropic properties particularly suited to their use as neuroleptic or anxiolytic agents. Thus, another aspect of the instant invention concerns a process for ameliorating a psychotic or an anxiety state in a mammal in need of such treatment which comprises systemic administration to said mammal an effective dose of from about 0.01 to 40 mg/kg body weight of a Formula (I) compound or a pharmaceutically acceptable acid addition salt thereof.

The term systemic administration as used herein refers to oral, rectal, and parenteral (i.e., intramuscular, intravenous, and subcutaneous) routes. Generally, it will be found that when a compound of the present invention is administered orally which is the preferred route, a larger quantity of the active agent is required to produce the same effect as a smaller quantity given parenterally. In accordance with good clinical practice, it is preferred to administer the instant compounds at a concentration level that will produce effective neuroleptic (anti-psychotic) or anxiolytic effects without causing any harmful or untoward side effects.

Therapeutically, the instant compounds are generally given as pharmaceutical compositions comprised of an effective anti-psychotic or anxiolytic amount of a compound of Formula I or a pharmaceutically acceptable acid addition salt thereof and a pharmaceutically acceptable carrier. Pharmaceutical compositions which provide from about 1 to 500 mg. of the active ingredient per unit dose are preferred and are conventionally prepared as tablets, lozenges, capsules, powders, aqueous or oily suspensions, syrups, elixirs and aqueous solutions.

Preferred oral compositions are in the form of tablets or capsules and may contain conventional excipients such as binding agents (e.g. syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethyleneglycol or silica), disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.01% to 10% by weight of the active compound in water or a vehicle consisting of a polyhydric aliphatic alcohol such as glycerine, propylene glycol, and polyethyleneglycols or mixtures thereof. The polyethyleneglycols consist of a mixture of non-volatile, normally liquid, polyethyleneglycols which are soluble in both water and organic liquids and which have molecular weights of from about 200 to 1500.

The following non-limiting examples serve to illustrate preparation of specific compounds of the instant inventions.

EXAMPLE 1

8-[4-[4-(3-Chlorophenyl)-1-piperazinyl]butyl]-6-thia-8-azaspiro[4.4]nonane-7,9-dione Dihydrochloride (Ia, Z=3-chlorophenyl)

(a) 5-Spirocyclopentyl-2,4-thiazolidindione Sodium Salt.

5-Spirocyclopentyl-2,4-thiazolidindione obtained according to Jones, et al., supra. (1.71 g., 0.01 mole) and 10 ml. of 1.0N sodium hydroxide (0.01 mole) are mixed and warmed as necessary to effect solution. Concentration of the basic solution with repeated acetone trituration and removal of solvent in vacuo affords 1.66 g. (86% yield) of the sodium salt of 5-spirocyclopentyl-2,4-thiazolidindione, m.p. 243°–245° C.

(b) 3-(4-Bromobutyl)-5-spirocyclopentyl-2,4-thiazolidindione.

5-Spirocyclopentyl-2,4-thiazolidindione sodium salt (3.83 g., 0.019 mole) in 180 ml. of dimethylformamide is slowly added to 1,4-dibromobutane (12.84 g., 0.059 mole) in 20 ml. of dimethylformamide. The mixture is stirred at room temperature for a 16 hr. period and then concentrated under reduced pressure. Residual material dissolved in chloroform, filtered and the filtrate concentrated and distilled affords 4.96 g. (85% yield) of 3-(4-bromobutyl)-5-spirocyclopentyl-2,4-thiazolidinedione, b.p. 122°–126° C. at 0.04 mmHg.

(c) 8-[4-[4-(3-Chlorophenyl)-1-piperazinyl]butyl]-6-thia-8-azaspiro[4.4]nonane-7,9-dione Dihydrochloride.

A mixture of 3-(4-bromobutyl)-5-spirocyclopentyl-2,4-thiazolidinedione (1.62 g., 0.005 mole), 1-(3-chlorophenyl)piperazine (1.04 g., 0.005 mole), potassium carbonate (0.8 g., 0.006 mole), and potassium iodide (0.09 g., 0.0006 mole), in 50 ml. of acetonitrile is heated under reflux for a 16 hr. period. The reaction mixture is cooled, filtered, and the filtrate concentrated in vacuo. Residual material is dissolved in chloroform, filtered, and the filtrate concentrated to afford 2.35 g. of the product as free base which, converted to the hydrochloride salt in acetonitrile, provides 1.29 g., (46%) of 8-[4-[4-(3-chlorophenyl)-1-piperazinyl]butyl]-6-thia-8-azaspiro[4.4]-7,9-dione dihydrochloride, m.p. 166.5°–171° C.

Anal. Calcd. for $C_{21}H_{28}ClN_3O_2S \cdot 2HCl$ (percent): C, 50.97; H, 6.11; N, 8.49. Found (percent): C, 51.32; H, 6.18; N, 8.58.

EXAMPLE 2

2-[4-[4-(7,9-Dioxo-6-thia-8-azaspiro[4.4]nonan-8-yl)butyl]-1-piperazinyl]pyridine-3-carbonitrile Hydrochloride (Ib, Z=3-cyano-2-pyridinyl)

(a) 1-(3-Cyano-2-pyridinyl)piperazine.

A mixture of 2-chloro-3-cyanopyridine (13.86 g., 0.1 mole) and piperazine (43.25 g., 0.5 mole) in ethanol is stirred for a period of 16 hr. at room temperature. The solvent is removed under reduced pressure and residual material dissolved in water and made basic with sodium hydroxide. The basified solution is extracted with ether and the ethereal extract dried and concentrated in vacuo to afford a cream colored solid. Extraction of this material with about 400 ml. of hot n-hexane and partial concentration of the extract and cooling affords 5.2 g. (28% yield) of 1-(3-cyano-2-pyrimidinyl)piperazine.

(b) 2-[4-[4-(7,9-Dioxo-6-thia-8-azaspiro[4.4]nonan-8-yl)butyl]-1-piperazinyl]pyridine-3-carbonitrile Hydrochloride.

Reaction of 3-(4-bromobutyl)-5-spirocyclopentyl-2,4-thiazolidinedione (4.96 g. 0.016 mole) with 1-(3-cyano-2-pyridinyl)piperazine (3.04 g., 0.016 mole), potassium carbonate (2.46 g., 0.018 mole) and potassium iodide (0.3 g., 0.0018 mole) in 125 ml. of acetonitrile according to the procedure of Example 1(c) provides the free base product which is converted to the hydrochloride salt in ethyl acetate with ethanolic hydrogen chloride. Crystallization of the hydrochloride salt from acetonitrile affords a 42% yield of 2-[4-[4-(7,9-dioxo-6-thia-8-azaspiro[4.4]nonan-8-yl)butyl]-1-piperazinyl]pyridine-3-carbonitrile hydrochloride, m.p. 207°–208° C.

Anal. Calcd. for $C_{21}H_{27}N_5O_2S\cdot HCl$ (percent): C, 56.5; H, 6.27; N, 15.56. Found (percent): C, 55.92; H, 6.24; N, 15.51.

EXAMPLE 3

8-[4-[4-(3-Trifluorophenyl)-1-piperazinyl]butyl]-6-thia-8-azaspiro[4.4]nonane-7,9-dione (Ic, Z=trifluorophenyl)

Reaction of 3-(4-bromobutyl)-5-spirocyclopentyl-2,4-thiazolidinedione with 1-(3-trifluorophenyl)piperazine according to the procedure of Example 1(c) affords the title compound.

EXAMPLE 4

8-[4-[4-(3-Methylphenyl)-1-piperazinyl]butyl]-6-thia-8-azaspiro[4.4]nonane-7,9-dione (Id, Z=3-methylphenyl)

Reaction of 3-(4-bromobutyl)-5-spirocyclopentyl-2,4-thiazolidinedione with 1-(3-methylphenyl)piperazine according to the procedure of Example 1(c) affords the title compound.

EXAMPLE 5

8-[4-[4-(2-Methylphenyl)-1-piperazinyl]butyl]-6-thia-8-azaspiro[4.4]nonane-7,9-dione (Ie, Z=2-methylphenyl)

Rection of 3-(4-bromobutyl)-5-spirocyclopentyl-2,4-thiazolidinedione and 1-(2-methylphenyl)piperazine according to the procedure of Example 1(c) affords the title compound.

EXAMPLE 6

8-[4-[4-(3-Methoxyphenyl)-1-piperazinyl]butyl]-6-thia-8-azaspiro[4.4]nonane-7,9-dione (If, Z=3-methoxyphenyl)

Reaction of 3-(4-bromobutyl)-5-spirocyclopentyl-2,4-thiazolidinedione and 1-(3-methoxyphenyl)piperazine according to the procedure of Example 1(c) affords the title compound.

What is claimed is:

1. A spirothiazolidinedione of Formula I

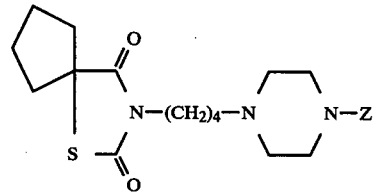

(I)

wherein Z is a $R_1$-substituted phenyl having the formula

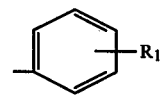

in which $R_1$ is hydrogen, halogen, lower alkyl of 1 to 4 carbon atoms, lower alkoxy of 1 to 4 carbon atoms or trifluoromethyl, a $R_2$-substituted 2-pyridinyl radical having the formula

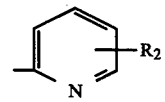

in which $R_2$ is hydrogen or cyano, or a pharmaceutically acceptable nontoxic acid addition salt thereof.

2. The compound of claim 1 which is 8-[4-[4-(3-chlorophenyl)-1-piperazinyl]butyl]-6-thia-8-azaspiro[4.4]nonane-7,9-dione or a pharmaceutically acceptable acid addition salt thereof.

3. The compound of claim 1 which is 8-[4-[4-(3-chlorophenyl)-1-piperazinyl]butyl]-6-thia-8-azaspiro[4.4]nonane-7,9-dione dihydrochloride.

4. The compound of claim 1 which is 2-[4-[4-(7,9-dioxo-6-thia-8-azaspiro[4.4]nonane-8-yl)butyl]-1-piperazinyl]pyridine-3-carbonitrile or a pharmaceutically acceptable acid addition salt thereof.

5. The compound of claim 1 which is 2-[4-[4-(7,9-dioxo-6-thia-8-azaspiro[4.4]nonane-8-yl)butyl]-1-piperazinyl]pyridine-3-carbonitrile hydrochloride.

* * * * *